United States Patent [19]

Collonges et al.

[11] Patent Number: 5,489,592
[45] Date of Patent: Feb. 6, 1996

[54] 3,4-DIHYDRO-4-OXO-3-(2-PROPENYL)-1-PHTHALAZINEACETIC ACIDS AND DERIVATIVES, THEIR PREPARATIONS AND MEDICINES CONTAINING THEM

[75] Inventors: François Collonges, Beynost; Hervé Dumas, Vaulx-Milieu; Philippe Durbin, Villeurbanne; Daniel Guerrier, Saint Genis Laval, all of France

[73] Assignee: Lipha, Lyonnaise Industrielle Pharmaceutique, Lyons, France

[21] Appl. No.: 211,427

[22] PCT Filed: Oct. 2, 1992

[86] PCT No.: PCT/FR92/00920

§ 371 Date: Jun. 20, 1994

§ 102(e) Date: Jun. 20, 1994

[87] PCT Pub. No.: WO93/07109

PCT Pub. Date: Apr. 15, 1993

[30] Foreign Application Priority Data

Oct. 7, 1991 [FR] France ................. 91 12299

[51] Int. Cl.⁶ ............ A61K 31/50; C07D 237/32; C07D 409/06
[52] U.S. Cl. .......................... 514/248; 544/237
[58] Field of Search .............. 544/237; 514/248

[56] References Cited

FOREIGN PATENT DOCUMENTS

| | | |
|---|---|---|
| 2895 | 7/1979 | European Pat. Off. . |
| 295051 | 6/1987 | European Pat. Off. . |
| 322153 | 6/1989 | European Pat. Off. . |
| 436307 | 7/1991 | European Pat. Off. . |

OTHER PUBLICATIONS

Shatalov, Chem Abs 98, 89286 (1982).
Malamas, J Med Chem 34, 1492 (1991).
Drug Evaulations Annual 1993 p. 149.
Dialog Abstract 08497366–93207366 For Narayanan, S, J.
Ann. Clin Lab Sci 23 (2), 148 (1993).

Primary Examiner—Mark L. Berch
Attorney, Agent, or Firm—Oblon, Spivak, McClelland, Maier & Neustadt

[57] ABSTRACT

Novel 3,4-dihydro-4-oxo-3(prop-2-enyl)-1-phtalazineacetic acids and derivatives of formula (I)

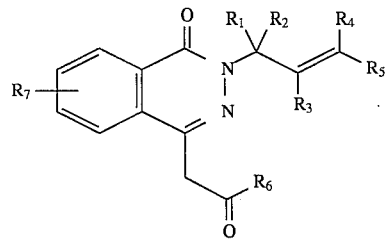

in which $R_1$ $R_2$ and $R_3$ are the same or different and stand for H, a halogen or a linear or branched aliphatic, saturated or unsaturated radical, substituted or not by at least one halogen or $R_4$ residue such as defined below, except when $R_4$ is H; $R_4$ and $R_5$ are the same or different and stand for H, a linear or branched aliphatic radical, saturated or unsaturated, an aryl or heteroaryl radical, said radicals being substituted or not by at least one grouping such as fluorine, chlorine, bromine, methyl or trifluoromethyl, where $R_4$ and $R_5$ do not simultaneously denote H; $R_6$ stands for hydroxy or alkoxy radical; $R_7$ stands for H, a halogen, a linear or branched aliphatic saturated or unsaturated radical, an alkoxy radical, said radicals being substituted or not by analiphatic or halogenated radical, a nitro group, a substituted or unsubstituted amino group, $S(O)n$ $R_8$ or a cyano group; n is equal to 0,1 or 2; $R_8$ is an aliphatic, linear or branched radical, an aryl or heteroaryl radical, an amino radical, said radicals being substituted or not by an aliphatic or halogenated radical. This invention also relates to the optional tautomeric forms of said acids and their pharmaceutically acceptable base addition salts. Also described is a process for preparing said compounds and the drugs containing same.

10 Claims, No Drawings

3,4-DIHYDRO-4-OXO-3-(2-PROPENYL)-1-PHTHALAZINEACETIC ACIDS AND DERIVATIVES, THEIR PREPARATIONS AND MEDICINES CONTAINING THEM

This Application is a 371 of PCT/FR92/00920, filed Oct. 20, 1992.

The present invention relates to new 3,4-dihydro-4-oxo-3-(2-propenyl)-1-phthalazineacetic acids, to processes which make it possible to prepare them and to their application in the therapeutic field and more particularly in the treatment of complications of diabetes such as cataracts, retinopathy, neuropathy and nephropathy.

Diabetes is characterized by a high glucose concentration in the blood. This glucose is normally metabolized by the enzyme hexokinase during the first stage of glycolysis, ending in degradation to pyruvate. When the glucose concentration is excessively high, the hexokinase is saturated and a second metabolic route comes into operation: the polyols route which involves two enzymes: aldose reductase, which converts glucose to sorbitol, and sorbitol dehydrogenase, which converts sorbitol to fructose. However, sorbitol is formed more rapidly than it is metabolized to fructose and therefore has a tendency to accumulate. This accumulation of sorbitol produces an intracellular osmotic pressure which can be sufficient to interfere with or destroy cell functions. Aldose reductase inhibitors are therefore useful in alleviating or preventing these effects of diabetes.

Numerous classes of products are described in the literature as in vitro aldose reductase inhibitors: the main ones are hydantoins, substituted acetic acids, flavonoids and anti-allergic compounds.

Only the first two classes have given clinically active products. In particular, in the class of acetic acids, Patent EP 2895 describes 3-benzyl-3,4-dihydro-4-oxo-1-phthalazineacetic acids having aldose reductase inhibiting properties, in which $R_1$, $R_2$ and $R_3$, which are identical or different, represent a hydrogen atom, a halogen atom or a $C_1$–$C_4$ alkyl group;

$R_4$ and $R_5$, which are identical or different, represent a hydrogen atom, a halogen atom, a $C_1$–$C_4$ alkyl group, a phenyl group, a phenyl group substituted by 1 to 5 substituents chosen from a halogen atom, a $C_1$–$C_4$ alkyl group and the trifluoromethyl group, or a heterocyclic group having from 3 to 10 carbon atoms including 1 to 4 heteroatoms chosen from N, S and O, optionally substituted by 1 to 5 substituents chosen from a halogen atom, a $C_1$–$C_4$ alkyl group and the trifluoromethyl group;

$R_6$ represents a hydroxyl or $C_1$–$C_4$ alkoxy group;

$R_7$ represents a hydrogen or halogen atom or a $C_1$–$C_4$ alkyl or $C_1$–$C_4$ alkoxy group, and to their pharmaceutically acceptable salts.

More recently, Patents EP 222,576, 295,051 and 322,153 describe oxophthalazineacetic acids having side chains of benzothiazole or heterocyclic type and having the property of inhibiting aldose reductase.

The present invention relates to new 3,4-dihydro-4-oxo-3-(2-propenyl)-1-phthalazineacetic acids and derivatives of formula I.

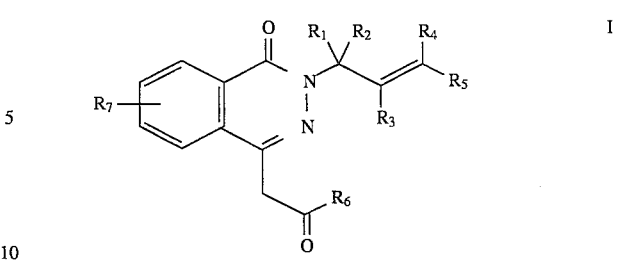

$C_1$–$C_4$ alkyl group is understood to mean groups containing a linear or branched chain, especially methyl, ethyl, propyl, isopropyl, butyl, isobutyl and tert-butyl groups.

$C_1$–$C_4$ alkoxy group is understood to mean groups containing a linear or branched chain, especially methoxy, ethoxy, propoxy, isopropoxy, butoxy, isobutoxy and tert-butoxy groups.

Halogen atom is understood to mean fluorine, chlorine, bromine or iodine atoms.

Heterocycle having from 3 to 10 atoms including 1 to 4 heteroatoms chosen from N, S and O is understood to mean mono- or bicyclic heterocycles, especially thienyl, benzothienyl, furyl, pyranyl, isobenzofuranyl, chromenyl, 2H-pyrrolyl, pyrrolyl, imidazolyl, pyrazolyl, pyridyl, pyrazinyl, pyrimidinyl, pyridazinyl, indolizinyl, isoindolyl, indolyl, 3H-indolyl, indazolyl, purinyl, quinolizinyl, isoquinolyl, quinolyl, phthalazinyl, naphthyridinyl, quinoxalinyl, quinazolinyl, cinnolinyl, pteridinyl, isothiazolyl, isoxazolyl, furazanyl, isochromanyl, chromanyl, pyrrolidinyl, $\Delta^2$-pyrrolinyl, imidazolidinyl, $\Delta^2$-imidazolinyl, pyrazolidinyl, $\Delta^3$-pyrazolinyl, piperidyl, piperazinyl, indolinyl, isoindolinyl and morpholinyl groups.

Advantageously, the $R_1$, $R_2$ and $R^3$ groups represent H, F or $CF_3$, the $R_6$ group represents OH or $OC_2H_5$ and the $R_7$ group represents H.

Mention may especially be made, among the preferred compounds, of those in which one of $R_4$ and $R^5$ represents a phenyl group, a phenyl group substituted by 1 to 5 substituents chosen from a halogen atom, a $C_1$–$C_4$ alkyl group and the trifluoromethyl group, or a heterocyclic group having from 3 to 10 atoms including 1 to 4 heteroatoms chosen from N, S and O, optionally substituted by 1 to 5 substituents chosen from a halogen atom, a $C_1$–$C_4$ alkyl group and the trifluoromethyl group, the other being H or $C_1$–$C_4$ alkyl, the $R_4$ or $R_5$ groups, when they represent a heterocycle, being especially a 5-membered heterocycle containing a single heteroatom, such as thienyl, pyrrolyl or furyl, preferably thienyl.

Mention may especially be made, among the preferred compounds, of (E) -3-[3-[2-fluoro-3-(trifluoromethyl)phenyl]- 2-propenyl]-3,4-dihydro-4-oxo-1-phthalazineacetic acid, (Z) -3-[2-fluoro-3-[3-(trifluoromethyl)phenyl]- 2-propenyl]-3,4-dihydro-4-oxo-1-phthalazineacetic acid, (E) -3-[3-(2,3,5-trifluorophenyl)-2-propenyl]-3,4-dihydro-4-oxo-1-phthalazineacetic acid, (E) -3-[3-(2,3,6-trifluorophenyl)-2-propenyl]-3,4-dihydro-4-oxo-1-phthalazineacetic acid, (E) -3-[3-(3-bromo-2,6-difluorophenyl)- 2-propenyl]-3,4-dihydro-4-oxo-1-phthalazineacetic acid, (E) -3-[3-[2,6-difluoro-3-(trifluoromethyl)phenyl]-2-propenyl]-3,4-dihydro-4-oxo-1-phthalazineacetic acid, (E) -3-[3-(2,3,5,6-tetrafluorophenyl)-2-propenyl]-3,4-dihydro- 4-oxo-1-phthalazineacetic acid or (Z) -3-[2-fluoro-3-[2-fluoro-3-(trifluoromethyl)phenyl]-2-propenyl]-3,4-dihydro-4-oxo-1-phthalazineacetic acid.

The possible tautomeric forms of the compounds of formula I are an integral part of the invention.

The addition salts with pharmaceutically acceptable bases of compounds of formula I in which $R_6$ is a hydroxyl radical are also an integral part of the invention, for example an alkali metal or alkaline-earth metal salt, such as a sodium, potassium, calcium or magnesium salt, an aluminium salt, an ammonium salt or a salt of an organic base contributing a pharmaceutically acceptable cation.

The compounds of the invention can be prepared according to the following methods:

(A) A compound of formula II

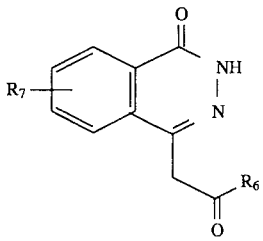

in which $R_6$ is an alkoxy group and $R_7$ has the meanings defined above, is reacted with a halide of formula III

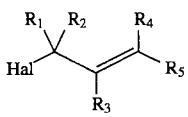

in which Hal is a chlorine, bromine or iodine atom and $R_1$, $R_2$, $R_3$, $R_4$ and $R_5$ have the meanings defined above, in the presence of a suitable base.

The process is preferably carried out in a solvent, for example dioxane, tetrahydrofuran (THF), dimethylformamide or dimethyl sulphoxide, and is advantageously accelerated by heating in the range from 40° to 110° C.

A particularly suitable base is, for example, an alkali metal hydride, amide or alkoxide, such as a sodium or potassium hydride, amide or alkoxide.

(B) The compounds of formula I in which $R_6$ is an alkoxy group are hydrolyzed in the presence of an acid or a base, for example an inorganic acid such as hydrochloric acid or an inorganic base such as an alkali metal hydroxide or carbonate, such as sodium or potassium hydroxide or carbonate.

Hydrolysis is generally carried out in the presence of water or of a solvent, for example acetic acid, methanol, ethanol or dioxane. It can be carried out at room temperature but is advantageously accelerated by heating in the range from 35° to 110° C.

The compounds of formula III can be obtained according to following Methods C, D or E:

(C) A hydroxylated compound of formula IV

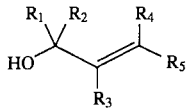

in which $R_1$, $R_2$, $R_3$, $R_4$ and $R_5$ have the meanings defined above, is treated with a halogenating agent according to processes well known in organic chemistry to give the corresponding compound of formula III. This halogenating agent can be an inorganic acid, such as hydrochloric acid or hydrobromic acid, or an agent such as thionyl chloride or bromide, sulphuryl chloride or bromide, phosphorus trichloride or tribromide, phosphorus pentachloride or pentabromide or phosphoryl chloride, or a halogen, such as chlorine, bromine or iodine, in the presence of triphenylphosphine.

The reaction can be carried out with or without solvent, it being possible for the solvent to be, for example, ether, dioxane, methylene chloride, chloroform, carbon tetrachloride, 1,2-dichloroethane, benzene or toluene.

The reaction can be carried out in the presence or in the absence of an organic base which is used to neutralize the inorganic acid formed, it being possible for this base to be, for example, pyridine or triethylamine.

(D) A hydroxylated compound of formula V

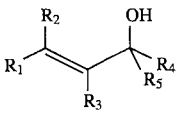

in which $R_1$, $R_2$, $R_3$, $R_4$ and $R_5$ have the meanings defined above, is treated with a halogenating agent analogous to those cited in Process (C), except for a halogen in the presence of triphenylphosphine. The compound of formula III is obtained via an allylic rearrangement well known in organic chemistry (see, for example, H. Burton and C. K. Ingold, J. Chem. Soc., 1928, 904).

(E) A compound of formula VI

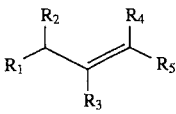

in which $R_1$, $R_2$, $R_3$, $R_4$ and $R_5$ have the meanings defined above, is treated with a halogenating agent such as N-chloro-, N-bromo- or N-iodosuccinimide, in a solvent such as carbon tetrachloride, in the presence or in the absence of a radical-generating compound such as azobisisobutyronitrile, at a temperature ranging from room temperature to the reflux temperature of the solvent.

The compounds of formula IV can themselves be prepared according to following Methods F or G:

(F) A compound of formula VII

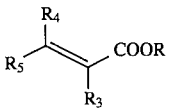

in which $R_3$, $R_4$ and $R_5$ have the meanings defined above and R is a lower alkyl group, is treated with a metal hydride such as lithium aluminium hydride, diisobutylaluminium hydride, lithium, sodium or potassium borohydride, or the $BH_3.Me_2S$ complex, or with a compound of formula VIII $$R_1\text{—MgBr} \qquad \text{VIII}$$

in which $R_1$ has the meaning defined above, in an aprotic solvent such as ether, tetrahydrofuran, dioxane, benzene, toluene or hexane.

(G) A compound of formula IX

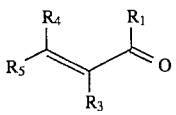

in which $R_1$, $R_3$, $R_4$ and $R_5$ have the meanings defined above, is treated with a metal hydride such as lithium aluminium hydride or lithium, sodium or potassium borohydride or with a compound of formula X $$R_2\text{—MgBr} \qquad \text{X}$$

in which $R_2$ has the meaning defined above, in a solvent such as ether, tetrahydrofuran, dioxane, benzene, toluene or hexane or, in the case of the action of a borohydride, methanol or ethanol.

The compounds of formula V can themselves be prepared according to following Methods H or I:

(H) A compound of formula XI

   XI in which $R_4$ and $R_5$ have the meanings defined above, is treated with a compound of formula XII

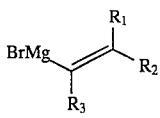   XII in which $R_1$, $R_2$ and $R_3$ have the meanings defined above, in a solvent such as ether, tetrahydrofuran, dioxane, benzene, toluene or hexane.

(I) A compound of formula XIII

   XIII in which $R_5$ has the meaning defined above, is treated with a compound of formula XIV

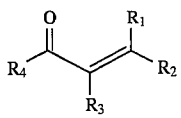   XIV in which $R_1$, $R_2$, $R_3$ and $R_4$ have the meanings defined above, in a solvent such as ether, tetrahydrofuran, dioxane, benzene, toluene or hexane.

The compounds of formula VI can themselves be prepared according to following Methods J and K:

(J) A compound of formula XI is treated with a compound of formula XV

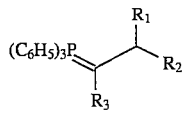   XV in which $R_1$, $R_2$ and $R_3$ have the meanings defined above, in a solvent such as tetrahydrofuran or hexane, at a temperature which can range from −30° C. to 40° C., to give the mixture of the E and Z isomers of a compound of formula VI.

(K) The mixture of the E and Z isomers of a compound of formula VI in which $R_3$ and $R_4$ are hydrogen is treated with a catalytic amount of iodine in a solvent such as hexane to give the E isomer alone of the compound of formula VI in which $R_3$ and $R_4$ are hydrogen.

The compounds of formula VII can themselves be prepared according to one of following Methods L, M or N:

(L) A compound of formula XVI

   XVI in which $R_5$ has the meaning defined above, is treated with malonic acid in the presence of pyridine and piperidine to give an ethylenic acid of formula XVII

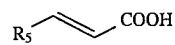   XVII which is esterified to an ester of formula VII in which $R_3$ and $R_4$ are hydrogen according to processes well known in organic chemistry.

(M) A compound of formula XI is treated with a compound of formula XVIII

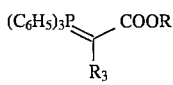   XVIII in which $R_3$ and R have the meanings defined above, in a solvent such as tetrahydrofuran or 1,2-dimethoxyethane, at a temperature which can range from room temperature to the reflux temperature of the solvent.

(N) A compound of formula XIX

   XIX in which $R_5$ is an aryl group defined above, is treated with a compound of formula XX

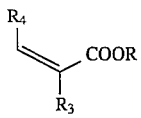   XX in which $R_3$, $R_4$ and R have the meanings defined above, in the presence of palladium acetate, triphenylphosphine and triethylamine, in a solvent such as benzene, toluene or triethylamine, at a temperature which can range from 80° C. to the reflux temperature of the solvent.

The compounds of formula XI can themselves be prepared according to one of following Methods P or Q.

(P) A compound of formula XXI

   XXI in which $R_5$ is an aryl group defined above, is treated with aqueous formic acid in the presence of Raney nickel at a temperature which can range from room temperature to the reflux temperature of the solvent to give an aldehyde of formula XI

   XI in which $R_4$ is equal to hydrogen.

(Q) A compound of formula XXII

   XXII in which $R_5$ is an aryl group defined above, is treated with hexamethylenetetramine in a mixture of acetic acid and water at a temperature which can range from room temperature to the reflux temperature of the solvent and is then treated with an inorganic acid such as hydrochloric acid in the same solvent, at a temperature equal to the reflux temperature of the solvent, to give a compound of formula XI

   XI in which $R_4$ is equal to hydrogen.

The compounds of formula XXII can themselves be prepared by following Process R:

(R) A compound of formula XXIII

   XXIII in which $R_5$ is an aryl group defined above, is treated with a halogenating agent according to a process analogous to that of Method E to give a compound of formula XXII.

The compounds of formula VII can also be prepared by following Process S:

(S) A compound of formula XXIV $$R_5-MgBr \qquad XXIV$$

in which $R_5$ is an aryl group defined above, is treated with the lithium salt of 3,3-difluoro-2-propenoic acid (prepared according to J. P. Gillet, R. Sauvetre and J. F. Normant, Synthesis, 1982, 297) in a solvent such as ether, THF or hexane, at a temperature ranging from −100° to 0° C., preferably between −80° and −40° C., to give a compound of formula VII in which R and $R_3$ are equal to H and $R_4$ is a fluorine atom.

The base addition salts of the compounds of formula I in which $R_6$ is a hydroxyl radical can be prepared, for example, by following Process T:

(T) A compound of formula I in which $R_6$ is a hydroxyl radical is treated with a base such as sodium hydroxide, potassium hydroxide or ammonia or a pharmaceutically acceptable organic base, in a solvent such as methanol, ethanol, isopropanol or acetone, optionally in the presence of water, at a temperature which can range from room temperature to the reflux temperature of the solvent, to give the addition salt of the compounds of formula I.

The properties of inhibiting the enzyme aldose reductase and of preventing the accumulation of sorbitol can be revealed during standardized laboratory tests below:

1) In vitro study: inhibition of aldose reductase

The aldose reductase used is obtained from crystallins from male Wistar rats according to a modification of the method of S. Hayman et al. (Journal of Biological Chemistry, 240, p. 877, 1965). The enzymatic extract is diluted in a phosphate buffer in the presence of NADPH and of various concentrations of the products to be tested. The reaction is triggered by L-glyceraldehyde and the rate of reaction is measured by monitoring the disappearance of NADPH by spectrophotometry at 340 nm. The inhibition of the rate of reaction is calculated for each concentration of products and then the concentration necessary for a 50% inhibition ($IC_{50}$) is evaluated by linear interpolation.

2) In vivo study: reduction in the accumulation of sorbitol

Male Wistar rats, weighing 200 to 250 g, are made diabetic by intravenous injection of streptozotocin (60 mg/kg). They then receive an oral treatment of the products to be tested, in the form of a 10% suspension in gum arabic, 4 hours, 30 hours and 52 hours after injection of streptozotocin. Eighteen hours after the last oral treatment, the rats are stunned and decapitated and their crystallins are then withdrawn. After extraction, the level of sorbitol in the crystallins is measured according to the enzymatic method described by H. U. Bergmeyer (Methods of Enzymatic Analysis, edited by H. U. Bergmeyer, Academic Press, New York, 3, p. 1323, 1974).

Various doses of products are tested and the inhibitions are calculated with respect to a control batch of diabetic rats. The dose necessary for a 50% reduction in the level of sorbitol is then evaluated by linear interpolation. By way of example, the results obtained for some of the tested products are given in the following table:

| Products Example No. | In vitro inhibition of aldose reductase $IC_{50}$ (nM) | Reduction in the level of sorbitol $ED_{50}$ (mg/kg) |
|---|---|---|
| $B_1$ | 10.2 (9.8–10.6)* | 4.8 (3.7–6.3)* |
| $B_{38}$ | 8.9 (8.3–9.4) | 4.7 (3.8–5.7) |
| $B_{40}$ | 8.2 (7.9–8.3) | 6.1 (4.0–9.2) |
| $B_{41}$ | 8.6 (8.2–9.0) | 4.4 (3.6–5.4) |
| $B_{43}$ | 9.6 (9.0–10.3) | 5.8 (4.6–7.2) |
| $B_{49}$ | 8.4 (7.7–9.1) | 8.2 (5.3–12.8) |

*Confidence interval

The compounds of the invention can be used as medicines as inhibitors of aldose reductase and especially in the treatment of complications of diabetes such as cataracts, retinopathies, neuropathies and nephropathies. These medicines can be administered orally in the form of film-coated tablets, gelatin capsules or granules, intravenously in the form of an injectable solution, transdermally in the form of a transdermal adhesive device or locally in the form of an eye lotion, solution, cream or gel.

The active ingredient is combined with various pharmaceutical excipients. The daily doses can vary from 10 mg to 300 mg of active ingredient. Several pharmaceutical formulations are given below as examples, without implied limitation:

| | |
|---|---|
| Composition of a tablet<br>Active ingredient<br>Excipient: lactose, wheat starch,<br>polyvidone, talc, magnesium stearate. | 100 mg |
| Composition of a gelatin capsule<br>Active ingredient<br>Excipient: lactose, wheat starch,<br>talc, magnesium stearate. | 100 mg |
| Composition of an injectable solution ampoule<br>Active ingredient<br>Excipient: mannitol, water for<br>injectable preparation. | 200 mg |
| Composition of a cream (composition for 100 g of cream)<br>Active ingredient<br>Excipient: self-emulsifiable cetyl-<br>stearyl alcohol, cetylaryloctanoate,<br>nipasol, sorbic acid, propylene glycol,<br>carbopol. | 2 g |

The invention is illustrated by the following examples, given without implied limitation:

EXAMPLE $A_1$ (Method A)

Ethyl (E)-3-[3-[2-fluoro-3-(trifluoromethyl)phenyl]-2-propenyl]-3,4-dihydro-4-oxo-1-phthalazineacetate 64.8 g (1.62 mol) of a 60% suspension of sodium hydride in oil are added portionwise under a nitrogen atmosphere to a solution of 341.9 g (1.472 mol) of ethyl 3,4-dihydro-4-oxo-1-phthalazineacetate (prepared according to the process described in Patent EP 2895) in 5 l of anhydrous DMF, the temperature being maintained between 25° and 30° C. The addition lasts approximately one hour. The mixture is then heated for 30 minutes at 60° C. The mixture is cooled to room temperature and a mixture of 421.6 g (1.76 mol) of 1-(3-chloro-1-propenyl) -2-fluoro-3-(trifluoromethyl) benzene (prepared according to Example $D_1$) and 98 ml of anhydrous DMF is added over 30 min. The temperature rises to 38° to 40° C. The mixture is then heated for 3 hours at 60° C. and is then allowed to return to room temperature overnight. The mixture is poured into 7 l of water and extracted with 2 times 4 l of ethyl acetate. Washing is carried out with water, the organic phase is dried over $Na_2SO_4$, filtered and evaporated under vacuum and the solid obtained is recrystallized from a hexane/ethyl acetate (4/1) mixture. Weight obtained: 474.7 g (Yd.=74%) M.p.=104°–106° C.

N.M.R. (CDCl$_3$) δ=1.2 (3H, t), 3.95 (2H, s), 4.15 (2H, q), 5.0 (2H, d), 6.4 to 6.8 (2H, m), 6.9 to 8.7 (7H, m).

EXAMPLES $A_2$ $A_{57}$

By using a process analogous to that of Example $A_1$, the compounds of Table I are obtained.

TABLE I

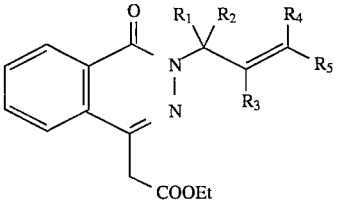

| Example | $R_1$ | $R_2$ | $R_3$ | $R_4$ | $R_5$ | Yd. | M.p. or N.M.R. |
|---|---|---|---|---|---|---|---|
| $A_2$ | H | H | H | H | $C_6H_5$ | 58% | 84–86° C. |
| $A_3$ | H | H | H | H | 2-F—$C_6H_4$ | 62% | $^1$H N.M.R. (CDCl$_3$). 1.2(3H, t); 3.9(2H, s); 4.15 (2H, q); 4.95 (2H, d); 6.4 to 8.6(10H, m) |
| $A_4$ | H | H | H | H | 3-F—$C_6H_4$ | 32% | $^1$H N.M.R. (CDCl$_3$): 1.2(3H, t); 3.9(2H, s); 4.15 (2H, q); 4.9 (2H, d); 6.3 to 8.5(10H, m) |
| $A_5$ | H | H | H | H | 4-F—$C_6H_4$ | 48% | 106–108° C. |
| $A_6$ | H | H | H | H | 2-Cl—$C_6H_4$ | 79% | $^1$H N.M.R. (CDCl$_3$): 1.2(3H, t); 3.95(2H, s); 4.15 (2H, q); 5.0 (2H, d); 6.0 to 8.6(10H, m) |
| $A_7$ | H | H | H | H | 3-Cl—$C_6H_4$ | 59% | $^1$H N.M.R. (CDCl$_3$): 1.2(3H, t); 3.95(2H, s); 4.15 (2H, q); 4.95 (2H, d); 6.4 to 8.6(10H, m) |
| $A_8$ | H | H | H | H | 4-Cl—$C_6H_4$ | 48% | 118–120° C. |
| $A_9$ | H | H | H | H | 2-Br—$C_6H_4$ | 59% | 104–106° C. |
| $A_{10}$ | H | H | H | H | 3-Br—$C_6H_4$ | 54% | 96–98° C. |
| $A_{11}$ | H | H | H | H | 4-Br—$C_6H_4$ | 47% | $^1$H N.M.R. (CDCl$_3$): 1.2(3H, t), 3.95(2H, s); 4.2 (2H, q); 4.95 (2H, d); 6.4 to 8.6(10H, m) |
| $A_{12}$ | H | H | H | H | 2-CF$_3$—$C_6H_4$ | 77% | $^1$H N.M.R. (CDCl$_3$): 1.2(3H, t); 3.95(2H, s); 4.2 (2H, q); 5.0 (2H, d); 6.0 to 8.6(10H, m) |
| $A_{13}$ | H | H | H | H | 3-CF$_3$—$C_6H_4$ | 48% | 110–112° C. |
| $A_{14}$ | H | H | H | H | 4-CF$_3$—$C_6H_4$ | 24% | $^1$H N.M.R. (CDCl$_3$): 1.2(3H, t); 3.95(2H, s); 4.15 (2H, q); 4.95 (2H, d), 6.4 to 8.6(10H, m) |
| $A_{15}$ | H | H | H | H | 2,3-F$_2$—$C_6H_3$ | 42% | 100–105° C. |
| $A_{16}$ | H | H | H | H | 2,4-F$_2$—$C_6H_3$ | 26% | $^1$H N.M.R. (CDCl$_3$): 1.2(3H, t); 3.95(2H, s); 4.15 (2H, q); 4.95 (2H, d); 6.3 to 8.6(9H, m) |
| $A_{17}$ | H | H | H | H | 2,5-F$_2$—$C_6H_3$ | 67% | $^1$H N.M.R. (CDCl$_3$): 1.2(3H, t); 3.95(2H, s); 4.15 |

TABLE I-continued

| Example | R₁ | R₂ | R₃ | R₄ | R₅ | Yd. | M.p. or N.M.R. |
|---|---|---|---|---|---|---|---|
| | | | | | | | (2H, q); 4.95 (2H, d); 6.3 to 8.6(9H, m) |
| $A_{18}$ | H | H | H | H | 2,6-F₂—C₆H₃ | 61% | ¹H N.M.R. (CDCl₃): 1.2(3H, t); 3.95(2H, s); 4.15 (2H, q); 4.95 (2H, d); 6.5 to 8.6(9H, m) |
| $A_{19}$ | H | H | H | H | 3,4-F₂—C₆H₃ | 23% | ¹H N.M.R. (CDCl₃): 1.2(3H, t): 3.95(2H, s); 4.15 (2H, q); 4.95 (2H, d); 6.2 to 8.6(9H, m) |
| $A_{20}$ | H | H | H | H | 3,5-F₂—C₆H₃ | 50% | 116–118° C. |
| $A_{21}$ | H | H | H | H | 2-F-3-C₆H₃ | 27% | 115–117° C. |
| $A_{22}$ | H | H | H | H | 2-F-6-Cl—C₆H₃ | 92% | ¹H N.M.R. (CDCl₃): 1.2(3H, t); 3.95(2H, s); 4.15 (2H, q); 5.0 (2H, d); 6.4 to 8.6(9H, m) |
| $A_{23}$ | H | H | H | H | 2-F-3-Br—C₆H₃ | 40% | 110–113° C. |
| $A_{24}$ | H | H | H | H | 2-F-4-Br—C₆H₃ | 38% | 121–123° C. |
| $A_{25}$ | H | H | H | H | 2-F-5-Br—C₆H₃ | 43% | 85° C. |
| $A_{26}$ | H | H | H | H | 3-Br-4-F—C₆H₃ | 37% | ¹H N.M.R. (CDCl₃): 1.2(3H, t); 3.95(2H, s); 4.15 (2H, q); 4.95 (2H, d); 6.3 to 8.6(9H, m) |
| $A_{27}$ | H | H | H | H | 3-Br-5-F—C₆H₃ | 46% | 125–127° C. |
| $A_{28}$ | H | H | H | H | 2,3-Cl₂—C₆H₃ | 10% | ¹H N.M.R. (CDCl₃): 1.2(3H, t); 3.95(2H, s); 4.15 (2H, q); 4.95 (2H, d); 6.3 to 8.6(9H, m) |
| $A_{29}$ | H | H | H | H | 2,6-Cl₂—C₆H₃ | 26% | ¹H N.M.R. (CDCl₃): 1.2(3H, t); 3.95(2H, s); 4.15 (2H, q); 5.0 (2H, d); 6.3 to 8.6(9H, m) |
| $A_{30}$ | H | H | H | H | 3,4-Cl₂—C₆H₃ | 52% | 108–110° C. |
| $A_{31}$ | H | H | H | H | 3,5-Cl₂—C₆H₃ | 37% | 120–122° C. |
| $A_{32}$ | H | H | H | H | 3,5-Br₂—C₆H₃ | 32% | 110–112° C. |
| $A_{33}$ | H | H | H | H | 2-Cl-3-CF₃—C₆H₃ | 35% | ¹H N.M.R. (CDCl₃): 1.2(3H, t); 3.95(2H, s); 4.15 (2H, q); 5.0 (2H, d); 6.0 to 8.6(9H, m) |
| $A_{34}$ | H | H | H | H | 3-CF₃-4-Cl—C₆H₃ | 42% | ¹H N.M.R. (CDCl₃): 1.2(3H, t); 3.95(2H, s); 4.15 (2H, q); 4.95 (2H, d); 6.4 to 8.6(9H, m) |
| $A_{35}$ | H | H | H | H | 2-F-5-CF₃—C₆H₃ | 34% | 77–79° C. |
| $A_{36}$ | H | H | H | H | 3,5-(CF₃)₂—C₆H₃ | 53% | 94–95° C. |
| $A_{37}$ | H | H | H | H | 2,3,5-F₃—C₆H₂ | 40% | 121–123° C. |
| $A_{38}$ | H | H | H | H | 2,3,6-F₃—C₆H₂ | 52% | 96–98° C. |
| $A_{39}$ | H | H | H | H | 2,5-F₂-3-Br—C₆H₂ | 23% | 124–126° C. |
| $A_{40}$ | H | H | H | H | 2,6-F₂-3-Br—C₆H₂ | 41% | 108–110° C. |
| $A_{41}$ | H | H | H | H | 2,6-F₂-3-CF₃—C₆H₂ | 45% | 92–94° C. |

TABLE I-continued

[Structure: 2-substituted benzoyl hydrazine with N-CH(R₁)(R₂)-C(R₃)=C(R₄)(R₅) side chain and ortho-CH=CH-COOEt group]

| Example | R₁ | R₂ | R₃ | R₄ | R₅ | Yd. | M.p. or N.M.R. |
|---|---|---|---|---|---|---|---|
| A₄₂ | H | H | H | H | 2,3-Cl₂-6-F—C₆H₂ | 63% | 94–95° C. |
| A₄₃ | H | H | H | H | 2,3,5,6-F₄—C₆H | 34% | ¹H N.M.R. (CDCl₃): 1.2(3H, t); 3.95(2H, s); 4.15 (2H, q):5.0 (2H, d); 6.3 to 8.6(7H, m) |
| A₄₄ | H | H | H | H | 2,5,6-F₃-3-Br—C₆H | 33% | 87–89° C. |
| A₄₅ | H | H | H | H | C₆F₅ | 38% | 110° C. |
| A₄₆ | CH₃ | H | H | H | 3,4-Cl₂—C₆H₃ | 26% | ¹H N.M.R. (CDCl₃): 1.2(3H, t); 1.6(3H, d); 4.0 (2H, s); 4.15 (2H, q); 5.6 to 8.6(10H, m) |
| A₄₇ | H | H | CH₃ | H | 2,4-Cl₂—C₆H₃ | 55% | ¹H N.M.R. (CDCl₃): 1.2(3H, t); 1.8(3H, s); 3.95 (2H, s); 4.15 (2H, q); 4.9 (2H, s); 6.3(1H, s); 7.0 to 8.6(7H, m) |
| A₄₈ | H | H | H | CH₃ | 3,4-Cl₂—C₆H₃ | 53% | ¹H N.M.R. (CDCl₃): 1.25(3H, t); 2.2(3H, s); 3.95 (2H, s); 4.15 (2H, q); 5.0 (2H, d); 6.0(1H, t); 7.0 to 8.6(7H, m) |
| A₄₉ | H | H | F | H | 3-CF₃—C₆H₄ | 65% | 109–111° C. |
| A₅₀ | H | H | F | 3-CF₃—C₆H₄ | H | 31% | 88–90° C. |
| A₅₁ | H | H | H | H | [2,5-disubstituted thiophene with CH₃] | 12% | ¹H N.M.R. (CDCl₃): 1.2(3H, t); 2.4(3H, s); 3.95 (2H, s); 4.15 (2H, q); 4.9 (2H, d); 6.0 to 8.6(8H, m) |
| A₅₂ | H | H | H | H | 2-F-3-Br—C₆H₃ | 6% | ¹H N.M.R. (CDCl₃): 1.2(3H, t); 3.5 to 3.7(2H, m); 3.95 (2H, s); 4.15(2H, q); 6.1 to 8.5(9H, m) |
| A₅₃ | H | H | H | F | 3-CF₃—C₆H₄ | 44% | 65–66° C. |
| A₅₄ | H | H | H | 3-CF₃—C₆H₄ | F | 28% | 79–81° C. |
| A₅₅ | H | H | F | H | 2-F-3-CF₃—C₆H₃ | 41% | 114–116° C. |
| A₅₆ | H | H | F | 2-F-3-CF₃—C₆H₃ | H | 44% | 88–90° C. |
| A₅₇ | H | H | H | 2-F-3-CF₃—C₆H₃ | H | | |

EXAMPLE B₁

(Method B)

(E) -3-[3-[2-fluoro-3-(trifluoromethyl)phenyl]-2-propenyl]-3,4-dihydro-4-oxo-1-phthalazineacetic acid A solution of 183.6 g (2.185 mol) of sodium bicarbonate in 4.2 l of water is rapidly added to a suspension of 474.4 g (1.092 mol) of ethyl (E) -3-[3-[2-fluoro-3-(trifluoromethyl)phenyl]-2-propenyl]-3,4-dihydro- 4-oxo-1-phthalazineacetate in 4.2 l of ethanol and heating is carried out for 2 h at reflux. A solution of 36.7 g (0.436 mol) of sodium bicarbonate in 800 ml of water is added and heating is carried out for 4 h 30 at reflux. 50 g of Norit are added and heating is carried out for a further 1 h at reflux. The mixture is filtered while hot through Hyflo and the ethanol is evaporated under vacuum. The residual aqueous phase is diluted with water to a volume of 10 l, cooled and acidified to pH=2 with 6N HCl (approximately 300 ml). The precipitate obtained is filtered, washed with water and dried under vacuum at 60° C. and then recrystallized from a hexane/ethyl acetate mixture to give a solid melting at 170°–172° C. Weight obtained: 382 g (Yd. 86%)

This product is purified by a further recrystallization from ethanol (Yd.=92%). M.p.=172°–173° C.

| Elemental analysis: $C_{20}H_{14}F_4N_2O_3$ (M = 406.335) | | | | |
|---|---|---|---|---|
|  | C % | H % | F % | N % |
| Calculated | 59.12 | 3.47 | 18.70 | 6.89 |
| Found | 55.98 | 3.38 | 18.48 | 6.99 |

$^1$H N.M.R. ($d_6$-DMSO): δ=4.0 (2H, s), 4.95 (2H, broad s), 6.7 (2H, broad s), 7.0 to 8.5 (7H, m), 12.7 (1H, s, exchangeable with $CF_3$-COOD).

EXAMPLES $B_2$ to $B_{57}$

By using a process analogous to that of Example $B_1$, the compounds of Table II are obtained.

TABLE II

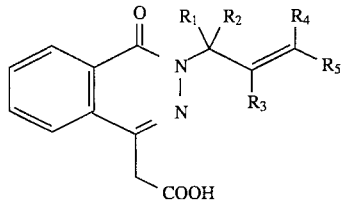

| Example | $R_1$ | $R_2$ | $R_3$ | $R_4$ | $R_5$ | Yd. (%) | M.p. (°C.) | Recrystallization solvent* |
|---|---|---|---|---|---|---|---|---|
| $B_2$ | H | H | H | H | $C_6H_5$ | 62% | 132–135 | EA |
| $B_3$ | H | H | H | H | 2-F—$C_6H_4$ | 76% | 170–172 | EA |
| $B_4$ | H | H | H | H | 3-F—$C_6H_4$ | 67% | 156–158 | EA |
| $B_5$ | H | H | H | H | 4-F—$C_6H_4$ | 76% | 150–152 | Hex/EA |
| $B_6$ | H | H | H | H | 2-Cl—$C_6H_4$ | 47% | 166–168 | EA + EtOH |
| $B_7$ | H | H | H | H | 3-Cl—$C_6H_4$ | 36% | 169–171 | EA |
| $B_8$ | H | H | H | H | 4-Cl—$C_6H_4$ | 71% | 162–164 | EA |
| $B_9$ | H | H | H | H | 2-Br—$C_6H_4$ | 66% | 163–165 | EA + EtOH |
| $B_{10}$ | H | H | H | H | 3-Br—$C_6H_4$ | 55% | 171–173 | EA + EtOH |
| $B_{11}$ | H | H | H | H | 4-Br—$C_6H_4$ | 34% | 179–181 | EA |
| $B_{12}$ | H | H | H | H | 2-$CF_3$—$C_6H_4$ | 52% | 160–162 | Hex/EA |
| $B_{13}$ | H | H | H | H | 3-$CF_3$—$C_6H_4$ | 58% | 167–169 | Hex/EA |
| $B_{14}$ | H | H | H | H | 4-$CF_3$—$C_6H_4$ | 59% | 182–185 | EA |
| $B_{15}$ | H | H | H | H | 2,3-$F_2$—$C_6H_3$ | 56% | 150–152 | Hex/EA |
| $B_{16}$ | H | H | H | H | 2,4-$F_2$—$C_6H_3$ | 58% | 150–152 | Hex/EA |
| $B_{17}$ | H | H | H | H | 2,5-$F_2$—$C_6H_3$ | 11% | 176–178 | Hex/EA |
| $B_{18}$ | H | H | H | H | 2,6-$F_2$—$C_6H_3$ | 74% | 172–174 | EA/EtOH |
| $B_{19}$ | H | H | H | H | 3,4-$F_2$—$C_6H_3$ | 63% | 157–159 | Hex/EA |
| $B_{20}$ | H | H | H | H | 3,5-$F_2$—$C_6H_3$ | 69% | 171–173 | Hex/EA |
| $B_{21}$ | H | H | H | H | 2-F-3-Cl—$C_6H_3$ | 60% | 169–171 | EA |
| $B_{22}$ | H | H | H | H | 2-F-6-Cl—$C_6H_3$ | 45% | 158–160 | Hex/EA |
| $B_{23}$ | H | H | H | H | 2-F-3-Br—$C_6H_3$ | 56% | 168–170 | EA |
| $B_{24}$ | H | H | H | H | 2-F-4-Br—$C_6H_3$ | 70% | 174–176 | EA/EtOH |
| $B_{25}$ | H | H | H | H | 2-F-5-Br—$C_6H_3$ | 46% | 183–185 | EA/EtOH |
| $B_{26}$ | H | H | H | H | 3-Br-4-F—$C_6H_3$ | 48% | 176–179 | EA |
| $B_{27}$ | H | H | H | H | 3-Br-5-F—$C_6H_3$ | 57% | 185–187 | EA |
| $B_{28}$ | H | H | H | H | 2,3-$Cl_2$—$C_6H_3$ | 44% | 160–162 | EA |
| $B_{29}$ | H | H | H | H | 2,6-$Cl_2$—$C_6H_3$ | 80% | 163–165 | EA |
| $B_{30}$ | H | H | H | H | 3,4-$Cl_2$—$C_6H_3$ | 66% | 164–166 | EA/EtOH |
| $B_{31}$ | H | H | H | H | 3,5-$Cl_2$—$C_6H_3$ | 59% | 196–197 | EA/EtOH |
| $B_{32}$ | H | H | H | H | 3,5-$Br_2$—$C_6H_3$ | 30% | 202–205 | EtOH/DMF |
| $B_{33}$ | H | H | H | H | 2-Cl-3-$CF_3$—$C_6H_3$ | 42% | 182–184 | EA |
| $B_{34}$ | H | H | H | H | 3-$CF_3$-4-Cl—$C_6H_3$ | 71% | 171–173 | Hex/EA |
| $B_{35}$ | H | H | H | H | 2-F-5-$CF_3$—$C_6H_3$ | 68% | 182–184 | Hex/EA |
| $B_{36}$ | H | H | H | H | 3,5-$(CF_3)_2$—$C_6H_3$ | 17% | 197–198 | Hex/EA |
| $B_{37}$ | H | H | H | H | 2,3,5-$F_3$—$C_6H_2$ | 30% | 171–173 | Hex/EA |
| $B_{38}$ | H | H | H | H | 2,3,6-$F_3$—$C_6H_2$ | 48% | 166–168 | EA |
| $B_{39}$ | H | H | H | H | 2,5-$F_3$-3-Br—$C_6H_2$ | 38% | 178–180 | Hex/EA |
| $B_{40}$ | H | H | H | H | 2,6-$F_3$-3-Br—$C_6H_2$ | 54% | 184–186 | EA/EtOH |
| $B_{41}$ | H | H | H | H | 2,6-$F_3$-3-$CF_3$—$C_6H_2$ | 60% | 174–176 | Hex/EA |
| $B_{42}$ | H | H | H | H | 2,3-$Cl_2$-6-F—$C_6H_2$ | 56% | 180–181 | Hex/EA |
| $B_{43}$ | H | H | H | H | 2,3,5,6-$F_4$—$C_6H$ | 47% | 180–182 | EA |
| $B_{44}$ | H | H | H | H | 2,5,6-$F_3$-3-Br—$C_6H$ | 44% | 185–187 | Hex/EA |
| $B_{45}$ | H | H | H | H | $C_6F_5$ | 74% | 181–183 | Hex/EA |
| $B_{46}$ | $CH_3$ | H | H | H | 3,4-$Cl_2$—$C_6H_3$ | 40% | 138–140 | Hex/EA |
| $B_{47}$ | H | H | $CH_3$ | H | 2,4-$Cl_2$—$C_6H_3$ | 53% | 153–154 | EA |
| $B_{48}$ | H | H | H | $CH_3$ | 3,4-$Cl_2$—$C_6H_4$ | 51% | 173–175 | EA |
| $B_{49}$ | H | H | F | H | 3-$CF_3$—$C_6H_4$ | 58% | 156–158 | Hex/EA |
| $B_{50}$ | H | H | F | 3-$CF_3$—$C_6H_4$ | H | 47% | 163–165 | Hex/EA |

TABLE II-continued

[Structure: benzoyl-N(R1R2R3)-CH=C(R4)R5 with ortho CH-N-COOH substituent]

| Example | R₁ | R₂ | R₃ | R₄ | R₅ | Yd. (%) | M.p. (°C.) | Recrystallization solvent* |
|---|---|---|---|---|---|---|---|---|
| B₅₁ | H | H | H | H | [2,5-dimethylthiophene via S, CH₃] | 25% | 106–108 | Hex/EA |
| B₅₂ | H | H | H | 2-F-3-Br—C₆H₃ | H | 15% | 177–179 | Hex/EA |
| B₅₃ | H | H | H | F | 3-CF₃—C₆H₄ | 36% | 166–168 | Hex/EA |
| B₅₄ | H | H | H | 3-CF₃—C₆H₄ | F | 37% | 168–170 | Hex/EA |
| B₅₅ | H | H | F | H | 2-F-3-CF₃—C₆H₃ | 13% | 157–159 | Hex/EA |
| B₅₆ | H | H | F | 2-F-3-CF₃—C₆H₃ | H | 22% | 174–176 | Hex/EA |
| B₅₇ | H | H | H | 2-F-3-CF₃—C₆H₃ | H | 22% | 174–176 | Hex/EA |

*EA = ethyl acetate, Hex = hexane, EtOH = ethanol, DMF = dimethylformamide

EXAMPLE C₁

(Method C)

(E)-1-Bromo-3-(3-bromo-1-propenyl)-5-fluorobenzene

A solution of 4.2 g (0.0182 mol) of (E)-3-(3-bromo-5-fluorophenyl)-2-propen-1-ol in 65 ml of anhydrous ether is cooled to 0° C. under a nitrogen atmosphere. 3.3 g (0.0121 mol) of phosphorus tribromide are added dropwise and then the mixture is stirred for 1 h at 0° C. and left to return to room temperature overnight. The mixture is poured into water and extraction with ether, washing with water, drying over sodium sulphate, filtration and concentration under vacuum are carried out.

The residue is used without subsequent purification in the following stage. Yield: 5.1 g (95%)

$^1$H N.M.R. (CDCl₃): δ=4.1 (2H, d), 6.3 to 6.5 (2H, m), 6.8 to 7.4 (3H, m).

EXAMPLES C₂ to C₁₅

By using a process analogous to that of Example C₁, the compounds of Table III are obtained.

TABLE III

[Structure: Br—C(R1R2)—C(R3)=C(R4)R5]

| Example | R₁ | R₂ | R₃ | R₄ | R₅ | Yd. | $^1$H N.M.R. (CDCl₃) |
|---|---|---|---|---|---|---|---|
| C₂ | H | H | H | H | 3-Br—C₆H₄ | 94% | 4.1(2H, d); 6.0 to 7.8 (6H, m) |
| C₃ | H | H | H | H | 2-F-4-Br—C₆H₃ | 91% | 4.1(2H, d); 6.2 to 7.4(5H, m) |
| C₄ | H | H | H | H | 3,4-Cl₂—C₆H₃ | 87% | 4.1(2H, d); 6.2 to 6.5(2H, m); 7.0 to 7.5(3H, m) |
| C₅ | H | H | H | H | 3-CF₃-4-Cl—C₆H₃ | 81% | 4.1(2H, d); 6.3 to 6.6(2H, m); 7.2 à 7.7(3H, m) |
| C₆ | CH₃ | H | H | H | 3,4-Cl₂—C₆H₃ | 70% | 1.85(3H, d); 4.5 to 5.0(1H, m); 6.3 to 6.5(2H, m); 6.9 to 7.5(3H, m) |
| C₇ | H | H | CH₃ | H | 2,4-Cl₂—C₆H₃ | 84% | 1.85(3H, s); 4.0(2H, s); 6.5 (1H, s); 6.9 to 7.4(3H, m) |
| C₈ | H | H | H | CH₃ | 3,4-Cl₂—C₆H₃ | 89% | |
| C₉ | H | H | F | H | 3-CF₃—C₆H₄ | 89% | 4.05(2H, d, J=19Hz); 5.8(1H, d, J=36Hz); 7.0 à 8.0(4H, m) |
| C₁₀ | H | H | F | 3-CF₃—C₆H₄ | H | 78% | 4.1(2H, d, J=22, 5Hz); 6.35(1H, d, J=17Hz); 7.48(4H, s) |

TABLE III-continued $$\underset{R_3}{\overset{R_1\;R_2\;\;R_4}{\underset{Br}{\bigg\backslash}\;\;\;\;\;\;\;\;R_5}}$$

| Example | $R_1$ | $R_2$ | $R_3$ | $R_4$ | $R_5$ | Yd. | 1H N.M.R. (CDCl$_3$) |
|---|---|---|---|---|---|---|---|
| $C_{11}$ | H | H | H | H | (2-methyl-5-methylthiophene group) | 90% | |
| $C_{12}$ | H | H | H | 3-CF$_3$—C$_6$H$_4$ | F | 98% | 4.0(2H, d, J=9Hz); 5.8(1H, dt, J$_1$=9Hz, J$_2$=18Hz); 7.0 to 7.9(4H, m) |
| $C_{13}$ | H | H | H | F | 3-CF$_3$—C$_6$H$_4$ | 98% | 4.2(2H, d, J=9Hz) 5.8(1H, dt, J$_1$=9Hz, J$_2$=33Hz); 7.1 to 7.9(4H, m) |
| $C_{14}$ | H | H | F | 2-F 3CF$_3$—C$_6$H$_3$ | H | 94% | 4.05(2H, d, J=21Hz); 6.4(1H, d, J=18Hz); 7.0 to 7.9(3H, m) |
| $C_{15}$ | H | H | F | H | 2-F-3-CF$_3$—C$_6$H$_3$ | 70% | 4.1(2H, d, J=19, 5Hz); 6.15(1H, d, J=34, 5Hz); 6.9 to 8.2(3H, m) |

EXAMPLE D$_1$ (Method D)

1-(3-Chloro-1-propenyl)-2-fluoro-3-(trifluoromethyl)benzene 334 ml of concentrated HCl are added over 10 minutes to a solution of 404.5 g (1.84 mol) of α-ethenyl-2-fluoro-3-(trifluoromethyl)benzenemethanol (prepared according to Example I$_1$) in 3.7 l of dioxane and the mixture is then heated for 2 h at reflux. 83.5 ml of concentrated HCl are added and the mixture is heated for a further 2 h at reflux.

The dioxane is evaporated under vacuum, the residue is diluted with 1 l of water, extraction is carried out with ether (3×800 ml), washing is carried out with water (2×800 ml), drying is carried out over Na$_2$SO$_4$, filtration is carried out, the ether is evaporated under vacuum and distillation is carried out. Weight obtained: 422.4 g (Yd.=96.3%) B.p.$_{0.4}$=69°–71° C. $^1$H N.M.R. (CDCl$_3$): δ=4.15 (2H, d), 6.0 to 7.8 (5H, m).

EXAMPLES D$_2$ to D$_{31}$

By using a process analogous to that of Example D$_1$, the compounds of Table IV are obtained.

TABLE IV $$\underset{R_3}{\overset{R_1\;R_2\;\;R_4}{\underset{Cl}{\bigg\backslash}\;\;\;\;\;\;\;\;R_5}}$$

| Example | $R_1$ | $R_2$ | $R_3$ | $R_4$ | $R_5$ | Yd. | $^1$H N.M.R. (CDCl$_3$) |
|---|---|---|---|---|---|---|---|
| D$_2$ | H | H | H | H | 2-F—C$_6$H$_4$ | 50% | 4.2(2H, d); 6.0 to 7.7 (6H, m) |
| D$_3$ | H | H | H | H | 3-F—C$_6$H$_4$ | 42% | 4.2(2H, d); 6.0 to 7.5 (6H, m) |
| D$_4$ | H | H | H | H | 4-Br—C$_6$H$_4$ | 63% | 4.2(2H, d); 6.0 to 7.6 (6H, m) |
| D$_5$ | H | H | H | H | 2-CF$_3$—C$_6$H$_4$ | 46% | 4.2(2H, d); 5.9 to 7.7 (6H, m) |
| D$_6$ | H | H | H | H | 2,3-F$_2$—C$_6$H$_3$ | 42% | 4.2(2H, d); 6.0 to 7.4 (5H, m) |
| D$_7$ | H | H | H | H | 2,4-F$_2$—C$_6$H$_3$ | 64% | 4.2(2H, d); 6.0 to 7.6 (5H, m) |
| D$_8$ | H | H | H | H | 2,5-F$_2$—C$_6$H$_3$ | 24% | 4.2(2H, d); 6.0 to 7.4 (5H, m) |
| D$_9$ | H | H | H | H | 2,6-F$_2$—C$_6$H$_3$ | 66% | 4.2(2H, d); 6.5 to 7.4 (5H, m) |
| D$_{10}$ | H | H | H | H | 3,4-F$_2$—C$_6$H$_3$ | 59% | 4.2(2H, d); 5.85 to 7.4 (5H, m) |
| D$_{11}$ | H | H | H | H | 3,5-F$_2$—C$_6$H$_3$ | 32% | 4.2(2H, d); 6.0 to 7.1 (5H, m) |
| D$_{12}$ | H | H | H | H | 2-F-3-Cl—C$_6$H$_3$ | 52% | 4.15(2H, d); 6.0 to 7.5 (5H, m) |
| D$_{13}$ | H | H | H | H | 2-F-6-Cl—C$_6$H$_3$ | 72% | 4.2(2H, d); 6.4 to 7.4 (5H, m) |
| D$_{14}$ | H | H | H | H | 2-F-3-Br-C$_6$H$_3$ | 53% | 4.2(2H, d); 6.1 to 7.6 (5H, m) |

TABLE IV-continued $$\underset{\underset{R_3}{|}}{\overset{\overset{R_1}{|}}{Cl}}C\overset{R_2}{\underset{|}{-}}C=C\overset{R_4}{\underset{R_5}{\diagdown}}$$

| Example | $R_1$ | $R_2$ | $R_3$ | $R_4$ | $R_5$ | Yd. | $^1$H N.M.R. (CDCl$_3$) |
|---|---|---|---|---|---|---|---|
| $D_{15}$ | H | H | H | H | 2-F-5-Br—C$_6$H$_3$ | 31% | E + Z Mixture 4.2(2H, d); 6.0 to 7.7 (5H, m) |
| $D_{16}$ | H | H | H | H | 3-Br-4-F—C$_6$H$_3$ | 35% | 4.2(2H, d); 5.9 to 7.6 (5H, m) |
| $D_{17}$ | H | H | H | H | 2,3-Cl$_2$—C$_6$H$_3$ | 61% | 4.2(2H, d); 5.9 to 7.5 (5H, m) |
| $D_{18}$ | H | H | H | H | 3,5-Cl$_2$—C$_6$H$_3$ | 46% | 4.15(2H, d); 6.2 to 6.5 (2H, m); 7.15(3H, s) |
| $D_{19}$ | H | H | H | H | 3,5-Br$_2$—C$_6$H$_3$ | 60% | 4.15(2H, d); 6.2 to 6.5 (2H, m); 7.1 to 7.6 (3H, m) |
| $D_{20}$ | H | H | H | H | 2-F-5-CF$_3$—C$_6$H$_3$ | 25% | 4.2(2H, d); 6.2 to 7.8 (5H, m) |
| $D_{21}$ | H | H | H | H | 2-Cl-3-CF$_3$—C$_6$H$_3$ | 39% | 4.2(2H, d); 6.0 to 6.5 (2H, m); 6.9 to 7.75 (3H, m) |
| $D_{22}$ | H | H | H | H | 3,5-(CF$_3$)$_2$—C$_6$H$_3$ | 19% | 4.2(2H, d); 6.4 to 8.5 (5H, m) |
| $D_{23}$ | H | H | H | H | 2,3,5-F$_3$—C$_6$H$_2$ | 36% | 4.2(2H, d); 6.0 to 7.4 (4H, m) |
| $D_{24}$ | H | H | H | H | 2,3,6-F$_3$—C$_6$H$_2$ | 81% | 4.2(2H, m); 6.5 to 7.4 (4H, m) |
| $D_{25}$ | H | H | H | H | 2,5-F$_2$-3-Br-C$_6$H$_2$ | 48% | 4.2(2H, d); 6.0 to 7.4 (4H, m) |
| $D_{26}$ | H | H | H | H | 2,6-F$_2$-3-Br—C$_6$H$_2$ | 84% | 4.2(2H, d); 6.0 to 7.6 (4H, m) |
| $D_{27}$ | H | H | H | H | 2,6-F$_2$-3-CF$_3$—C$_6$H$_2$ | 45% | 4.2(2H, d); 6.4 to 7.6 (4H, m) |
| $D_{28}$ | H | H | H | H | 2,3-Cl$_2$-6-F—C$_6$H$_2$ | 85% | 4.2(2H, d); 6.0 to 7.5 (4H, m) |
| $D_{29}$ | H | H | H | H | 2,3,5,6-F$_4$—C$_6$H | 29% | 4.2(2H, m); 6.5 to 7.3 (3H, m) |
| $D_{30}$ | H | H | H | H | 2,5,6-F$_3$-3-Br—C$_6$H | 37% | 4.2(2H, m); 6.0 to 7.6 (3H, m) |
| $D_{31}$ | H | H | H | H | C$_6$F$_5$ | 27% | 4.2(2H, m); 6.5 to 6.7 (2H, m) |

EXAMPLE E (Method E)

5-Bromo-1-(3-bromo-1-propenyl)-2-fluorobenzene

A mixture of 4.3 g (0.02 mol) of 5-bromo-2-fluoro-1-(1-propenyl) benzene, 100 ml of carbon tetrachloride, 0.07 g of azobisisobutyronitrile and 3.6 g (0.02 mol) of N-bromosuccinimide is heated for 5 h at reflux. The solid is filtered, the filtrate is evaporated under vacuum and the residue used without other purification in the following stage: Yd.: 5.4 g (91%)

$^1$H N.M.R. (CDCl$_3$): δ=4.15 (2H, d), 6.3 to 7.7 (5H, m).

EXAMPLE F$_1$ (Method F)

3-(4-Bromo-2-fluorophenyl)-2-propen-1-ol

A solution of 14.4 g (0.0555 mol) of methyl 3-(4-bromo-2-fluorophenyl -2-propenoate in 100 ml of anhydrous benzene is added dropwise to a suspension of 2.1 g (0.0553 mol) of LiAlH$_4$ in 80 ml of anhydrous benzene and the mixture is then progressively heated to 60° C. under a nitrogen atmosphere. The temperature is maintained between 60° and 65° C. for 10 min and the mixture is then heated for 12 h at reflux. The mixture is cooled in an ice bath, carefully hydrolysed, filtered, the inorganic materials are washed with toluene, the filtrate is evaporated under vacuum and the residue is purified by chromatography on silica (eluent: 1/1 hexane/ethyl acetate). Yd.: 9.8 g (76%) M.p.: 38°–40° C.

$^1$H N.M.R. (CDCl$_3$): δ=2.8 (1H, s, exchangeable with D$_2$O), 4.25 (2H, d), 6.0 to 7.5 (5H, m).

EXAMPLES F$_2$ and F$_3$

By using a process analogous to that of Example F$_1$, the compounds of Table V are obtained.

TABLE V $$\underset{\text{HO}}{\overset{R_1}{\phantom{|}}}\overset{R_2}{\underset{R_3}{\phantom{|}}}\overset{R_4}{=}\phantom{|}R_5$$

| Example | $R_1$ | $R_2$ | $R_3$ | $R_4$ | $R_5$ | Yd. | $^1$H N.M.R. (CDCl$_3$) |
|---|---|---|---|---|---|---|---|
| F$_2$ | H | H | CH$_3$ | H | 2,4-Cl$_2$—C$_6$H$_3$ | 99% | 1.7(3H, s), 2.0(1H, s, exchangeable with D$_2$O), 4.15(2H, s), 6.4(1H, s), 7.0 to 7.5 (3H, m) |
| F$_3$ | H | H | H | CH$_3$ | 3,4-Cl$_2$—C$_6$H$_3$ | 95% | 1.8(1H, s, exchangeable with CF$_3$—COOD), 2.0(3H, s), 4.3(2H, d), 5.9(1H, t), 7.0 to 7.5 (3H, m) |

EXAMPLE F$_4$ (Method F')

3-(3-Bromo-5-fluorophenyl)-2-propen-1-ol 56 ml (0.056 mol) of a 1M solution of diisobutylaluminium hydride in toluene are added dropwise under a nitrogen atmosphere to a suspension of 7.2 g (0.0278 mol) of methyl 3-(3-bromo-5-fluorophenyl)-2-propenoate in 84 ml of anhydrous ether cooled to 0° C. The mixture is stirred for 30 min at 0° C. and then for 3 h at room temperature. The mixture is cooled in an ice bath and carefully hydrolyzed with 6N H$_2$SO$_4$. Separation is carried out by settling and the organic phase is washed with water, dried over Na$_2$SO$_4$, filtered and evaporated under vacuum. The residue is purified by chromatography on silica (eluent: 2/1 hexane/ethyl acetate). Yd.: 4.2 g (65%)

$^1$H N.M.R. (CDCl$_3$): 1.95 (1H, s, exchangeable with D$_2$O), 4.28 (2H, d), 6.0 to 7.4 (5H, m).

EXAMPLES F$_5$ to F$_9$

By using a process analogous to that of Example F4, the compounds of Table VI are obtained.

TABLE VI $$\underset{\text{HO}}{\overset{R_1}{\phantom{|}}}\overset{R_2}{\underset{R_3}{\phantom{|}}}\overset{R_4}{=}\phantom{|}R_5$$

| Example | $R_1$ | $R_2$ | $R_3$ | $R_4$ | $R_5$ | Yd. | $^1$H N.M.R. (CDCl$_3$) |
|---|---|---|---|---|---|---|---|
| F$_5$ | H | H | H | H | 3-CF$_3$-4-Cl—C$_6$H$_3$ | 50% | 1.8(1H, s, exchangeable with D$_2$O), 4.3(2H, d), 6.3 to 6.6(2H, m), 7.2 to 7.7(3H, m) |
| F$_6$ | H | H | F | H | 3-CF$_3$—C$_6$—H$_4$ | 23% | 2.85(1H, s, exchangeable with CF$_3$—COOD), 4.2(2H, d, J=13Hz), 5.75(1H, d, J=38Hz), 7.1 to 7.8(4H, m) |
| F$_7$ | H | H | F | 3-CF$_3$—C$_6$H$_4$ | H | 44% | 2.5(1H, s, exchangeable with CF$_3$—COOD), 4.3(2H, d, J=21Hz), 6.3(1H, d, J=19Hz; 7.4(4H, s) |
| F$_8$ | H | H | F | H | 2-F-3-CF$_3$—C$_6$H$_3$ | 4.9% | 2.0(1H, s, exchangeable with D$_2$O), 4.3 (2H, d, J=13Hz), 6.1 (1H, d, J=38Hz); 6.9 to 8.2(3H, m) |
| F$_9$ | H | H | F | 2-F-3-CF$_3$—C$_6$H$_3$ | H | 27% | 2.15(1H, s, exchangeable with D$_2$O), 4.25 (2H, d, J=21 Hz), 6.32 (1H, d, J=19Hz), 7.0 to 7.9(3H, m) |

EXAMPLE F$_{10}$ (Method F")

3-Fluoro-3-[3-(trifluoromethyl)phenyl]-2-propen-1-ol 2.5 g (0.0106 mol) of 3-fluoro-3-[3-(trifluoromethyl)phenyl]-2-propenoic acid (E+Z) in 25 ml of THF are added dropwise to 6.5 ml (0.013 mol) of a 2M solution of BH$_3$.Me$_2$S complex in toluene, cooled to 10° C. The mixture is stirred for 24 h at room temperature. 1.6 ml (0.003 mol) of 2M solution of $BH_3.Me_2S$ in toluene are added and the mixture stirred for a further 3 h at room temperature. Hydrolysis is carried out carefully with 25 ml of ice-cold water. Extraction is carried out with ether, the extract is washed with water, dried over sulphate, filtered and evaporated under vacuum and the residue is purified by chromatography on silica (Hex/EA: 4/1). 0.4 g of E alcohol (Yd.: 17%, $^1$H N.M.R., $CDCl_3$:1.9 (1H, s), 4.2 (2H, m), 5.7 (1H, dt, $J_1$= 19.5 Hz, $J_2$=7.5 Hz), 7.1 to 7.9 (4H, m)) and 0.3 g of Z alcohol (Yd.: 13%, $^1$H N.M.R., $CDCl_3$:1.7 (1H, s), 4.4 (2h, dd), 5.65 (1H, dt, $J_1$=36 Hz, $J_2$=7.5 Hz), 7.1 to 7.9 (4H, m)) are obtained.

EXAMPLE G (Method G)

4-(3,4-Dichlorophenyl)-3-buten-2-ol 2.25 g (0.0599 mol) of $NaBH_4$ are added portionwise at room temperature to a suspension of 39.2 g (0.182 mol) of 4-(3,4-dichlorophenyl)-3-buten-2-one in 900 ml of ethanol and the mixture is stirred overnight at room temperature. The mixture is concentrated under vacuum, taken up in water, extracted with methylene chloride, washed with water, dried over sodium sulphate, filtered and evaporated under vacuum. The product obtained is used without subsequent purification in the following stage. Yd.: 35.2 g (89%)

$^1$H N.M.R. ($CDCl_3$): 1.35 (3H, d), 2.1 (1H, broad s, exchangeable with $CF_3COOD$), 4.2 to 4.7 (1H, m), 6.2 to 6.4 (2H, m), 6.9 to 7.6 (3H, m).

EXAMPLE $H_1$ (Method H)

α-Ethenyl-2-fluoro-5-(trifluoromethyl)benzenemethanol 52.6 ml (0.0526 mol) of a 1M solution of vinylmagnesium bromide in THF are added dropwise at a temperature below 25° C. to a solution of 10.1 g (0.0526 mol) of 2-fluoro-5-(trifluoromethyl)benzaldehyde (prepared according to Example P) in 53 ml of anhydrous THF. The mixture is then stirred for 2 h 30 at room temperature. Hydrolysis is carried out with a saturated aqueous $NH_4Cl$ solution while cooling between 10° and 20° C.; extraction is carried out with ether and the extract is washed with water, dried over $Na_2SO_4$, filtered and evaporated under vacuum. The residue is used without subsequent purification in the following stage. Yd.: 11.6 g (quantitative)

$^1$H N.M.R. ($CDCl_3$):2.3 (1H, broad s, exchangeable with $D_2O$), 4.7 to 6.5 (4H, m), 6.8 to 8.0 (3H, m).

EXAMPLES $H_2$ to $H_7$

By using a process analogous to Example $H_1$, the compounds of Table VII are obtained.

TABLE VII

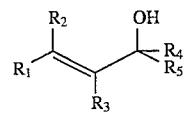

| Example | $R_1$ | $R_2$ | $R_3$ | $R_4$ | $R_5$ | Yd. | $^1$H N.M.R. ($CDCl_3$) |
|---|---|---|---|---|---|---|---|
| $H_2$ | H | H | H | H | 2-F-$C_6H_4$ | 99% | 2.8(1H, s, exchangeable with $D_2O$), 4.6 to 6.4 (4H, m), 6.8 to 7.8(4H, m) |
| $H_3$ | H | H | H | H | 3-F—$C_6H_4$ | 99% | 2.8(1H, s, exchangeable with $D_2O$), 4.6 to 6.4 (4H, m), 6.5 to 7.7(4H, m) |
| $H_4$ | H | H | H | H | 4-Br—$C_6H_4$ | 99% | 2.8(1H, s, exchangeable with $D_2O$), 4.5 to 6.3 (4H, m), 6.9 to 7.6(4H, m) |
| $H_5$ | H | H | H | H | 4-$CF_3$—$C_6H_4$ | 99% | 2.5(1H, s exchangeable with $CF_3COOD$), 4.6 to 6.3(4H, m), 7.0 to 7.8(4H, m) |
| $H_6$ | H | H | H | H | 2,3-$F_2$—$C_6H_3$ | 99% | 2.7(1H, s, exchangeable with $D_2O$), 4.6 to 6.3 (4H, m), 6.5 to 7.5(3H, m) |
| $H_7$ | H | H | H | H | 2,4-$F_2$—$C_6H_3$ | 99% | 2.9(1H, s, exchangeable with $D_2O$), 4.6 to 6.4 (4H, m), 6.5 to 7.6(3H, m) |
| $H_8$ | H | H | H | H | 2,5-$F_2$—$C_6H_3$ | 99% | 2.6(1H, s, exchangeable with $D_2O$), 4.6 to 6.3 (4H, m), 6.7 to 7.5(3H, m) |
| $H_9$ | H | H | H | H | 2,6-$F_2$—$C_6H_3$ | 99% | 2.45(1H, s, exchangeable with $D_2O$), 4.6 to 6.5 (4H, m), 6.3 to 7.3(3H, m) |
| $H_{10}$ | H | H | H | H | 3,4-$F_2$—$C_6H_3$ | 99% | 2.6(1H, s, exchangeable with $D_2O$), 4.55 to 6.3 (4H, m), 6.8 to 7.4(3H, m) |
| $H_{11}$ | H | H | H | H | 3,5-$F_2$—$C_6H_3$ | 99% | 2.3(1H, s, exchangeable with $D_2O$), 4.55 to 6.2 (4H, m), 6.3 to 7.3(3H, m) |
| $H_{12}$ | H | H | H | H | 2-F-3-Cl—$C_6H_3$ | 99% | 3.25(1H, s, exchangeable with $CF_3$—COOD), 4.6 to 6.4(4H, m), 6.6 to 7.8(3H, m) |

TABLE VII-continued $$\underset{R_3}{\overset{R_2}{\underset{R_1}{\diagdown}}C=C}\overset{OH}{\underset{}{\overset{|}{\underset{R_5}{-C-R_4}}}}$$

| Example | $R_1$ | $R_2$ | $R_3$ | $R_4$ | $R_5$ | Yd. | $^1$H N.M.R. (CDCl$_3$) |
|---|---|---|---|---|---|---|---|
| H$_{13}$ | H | H | H | H | 2-F-6-Cl—C$_6$H$_3$ | 99% | 2.5(1H, s, exchangeable with D$_2$O), 4.6 to 6.5 (4H, m), 6.6 to 7.4 (3H, m) |
| H$_{14}$ | H | H | H | H | 2-F-3-Br—C$_6$H$_3$ | 96% | 2.25(1H, s, exchangeable with D$_2$O, 4.6 to 6.4 (4H, m), 6.6 to 7.7(3H, m) |
| H$_{15}$ | H | H | H | H | 2-F-5-Br—C$_6$H$_3$ | 96% | 2.3(1H, s, exchangeable with D$_2$O), 4.6 to 6.4 (4H, m), 6.5 to 8.0(3H, m) |
| H$_{16}$ | H | H | H | H | 3-Br-4-F—C$_6$H$_3$ | 91% | 2.3(1H, s, exchangeable with D$_2$O), 4.5 to 6.3 (4H, m), 6.7 to 7.7(3H, m) |
| H$_{17}$ | H | H | H | H | 2,3-Cl$_2$—C$_6$H$_3$ | 99% | 2.75(1H, s exchangeable with CF$_3$—COOD), 4.6 to 6.3(4H, m), 6.9 to 7.7(3H, m) |
| H$_{18}$ | H | H | H | H | 2,6-Cl$_2$—C$_6$H$_3$ | 99% | 3.0(1H, s, exchangeable with CF$_3$—COOD), 4.8 to 6.6(4H, m), 6.9 to 7.5(3H, m) |
| H$_{19}$ | H | H | H | H | 3,5-Cl$_2$—C$_6$H$_3$ | 99% | 2.75(1H, s, exchangeable with D$_2$O), 4.5 to 6.3 (4H, m), 7.2(3H, s) |
| H$_{20}$ | H | H | H | H | 3,5-Br$_2$—C$_6$H$_3$ | 99% | 2.2(1H, s, exchangeable with CF$_3$—COOD), 4.5 to 6.3(4H, m), 7.0 to 7.7(3H, m) |
| H$_{21}$ | H | H | H | H | 2-F-3-CF$_3$—C$_6$H$_3$ | 91% | 2.6(1H, s, exchangeable with D$_2$O), 4.6 to 6.4 (4H, m), 6.9 to 7.9 (3H, m) |
| H$_{22}$ | H | H | H | H | 2-Cl-3-CF$_3$—C$_6$H$_3$ | 99% | 2.9(1H, s, exchangeable with CF$_3$—COOD 4.6 to 6.3 4H, m), 7.0 to 7.8 (3H, m) |
| H$_{23}$ | H | H | H | H | 3,5-(CF$_3$)$_2$—C$_6$H$_3$ | 55% | 2.85(1H, s, exchangeable with D$_2$O), 4.6 to 6.4 (4H, m), 7.75(3H, s) |
| H$_{24}$ | H | H | H | H | 2,5-F$_3$-3-Br—C$_6$H$_2$ | 98% | 2.25(1H, s, exchangeable with D$_2$O), 4.6 to 6.3 (4H, m), 6.9 to 7.3 (2H, m) |
| H$_{25}$ | H | H | H | H | 2,6-F$_3$-3-CF$_3$—C$_6$H$_2$ | 99% | 2.7(1H, s, exchangeable with CF$_3$—COOD), 4.5 to 6.4(4H, m), 6.6 to 7.8 (2H, m) |
| H$_{26}$ | H | H | H | H | 2,3,5,6-F$_4$—C$_6$H | 99% | 2.6(1H, d, exchangeable with CF$_3$—COOD), 4.6 to 6.4(4H, m), 6.6 to 7.4 (1H, m) |
| H$_{27}$ | H | H | H | H | C$_6$F$_5$ | 99% | 2.75(1H, s, exchangeable with D$_2$O), 4.6 to 6.5 (4H, m) |

EXAMPLE I$_1$ (Method I)

α-Ethenyl-2-fluoro-3-(trifluoromethyl)benzenemethanol

A solution of 360 g (2.194 mol) of 1-fluoro-2-trifluoromethylbenzene in 3.4 l of anhydrous THF is cooled to −70° C. under a nitrogen atmosphere. 1.508 l (2.412 mol) of a 1.6M solution of n-butyllithium in hexane are added dropwise over 70 minutes while maintaining the temperature below −67° C. and then the mixture is stirred for 30 minutes at −70° C. 154 ml (2.305 mol) of acrolein are then added dropwise over 30 min while maintaining the temperature below −60° C. The mixture is then stirred for 30 min at −70° C. The mixture is allowed to return to room temperature and is poured onto a mixture of 3.8 kg of ice and 300 ml of concentrated H$_2$SO$_4$.

Extraction with ether (3×800 ml), washing with water (3×800 ml), drying over Na$_2$SO$_4$, filtration, evaporation under vacuum and distillation are carried out. Weight obtained: 408.6 g (Yd.=84%) B.p.$_{0.2}$=70°–73° C. M.p.= 46°–47° C. IR =vOH=3350 cm$^{-1}$ $^1$H N.M.R. (CDCl$_3$): δ=2.35 (1H, s, exchangeable with D$_2$O), 5.0 to 6.4 (4H, m), 7.0 to 7.8 (3H, m).

EXAMPLES $I_2$ to $I_3$

By using a process analogous to that of Example $I_1$, the compounds of Table VIII are obtained.

TABLE VIII

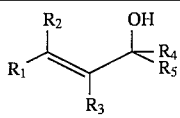

| Example | $R_1$ | $R_2$ | $R_3$ | $R_4$ | $R_5$ | Yd. | $^1$H N.M.R. (CDCl$_3$) |
|---|---|---|---|---|---|---|---|
| $I_2$ | H | H | H | H | 2-F-5-CF$_3$—C$_6$H$_3$ | 86% | 2.75(1H, s, broad s, exchangeable with D$_2$O), 4.7 to 6.5(4H, m), 6.8 to 8.0 (3H, m) |
| $I_3$ | H | H | H | H | 2,3,6-F$_3$—C$_6$H$_2$ | 96% | 2.8(1H, s, exchangeable with CF$_3$—COOD), 4.9 to 6.5(4H, m), 6.5 to 7.4 (2H, m) |
| $I_4$ | H | H | H | H | 2,6-F$_2$-3-C—F$_3$—C$_6$H$_2$ | 68% | 2.9(1H, s, exchangeable with D$_2$O), 4.9 to 6.5 (4H, m), 6.5 to 7.7(2H, m) |
| $I_5$ | H | H | H | H | 2,3-Cl$_2$-6-F—C$_6$H$_2$ | 78% | 2.65(1H, s exchangeable with D$_2$O), 5.0 to 6.5 (4H, m), 6.92(1H, dd, J$_1$=9Hz, J$_2$=9Hz), 7.35(1H, dd, J$_1$=6Hz, J$_2$=9Hz) |

EXAMPLE $I_6$ (Method I')

3-Bromo-α-ethenyl-2,6-difluorobenzenemethanol 121.1 ml (0.194 mol) of a 1.6M solution of n-butyllithium in hexane are added dropwise to a solution, cooled to −10° C., of 21.5 g (0.212 mol) of diisopropylamine in 194 ml of anhydrous THF. The mixture is stirred for 10 min at −10° C. under a nitrogen atmosphere, is then cooled to −76° C. and a solution of 37.4 g (0.194 mol) of 1-bromo-2,4-difluorobenzene in 270 ml of anhydrous THF is added dropwise over 30 minutes, at a temperature below −70° C. The mixture is stirred for 2 minutes at −70° C. and then a solution of 14.7 g (0.212 mol) of acrolein in 30 ml of anhydrous THF is added dropwise over 10 minutes at a temperature below −60° C. The mixture is then stirred for 30 minutes at -70° C., and the temperature is then allowed to return to 0° C. The mixture is poured onto a mixture of 350 g of ice and 35 ml of concentrated H$_2$SO$_4$. Extraction with ether, washing with water, drying over Na$_2$SO$_4$, filtration, evaporation under vacuum and distillation are carried out. Weight obtained: 29 g (Yd.=60%) B.p.$_{0.5}$=86°–88° C.

$^1$H N.M.R. (CDCl$_3$):δ=3.0 (1H, s, exchangeable with D$_2$O), 4.9 to 6.5 (4H, m), 6.5 to 7.6 (2H, m).

EXAMPLE $I_7$

3-Bromo-δ-ethenyl-2,5,6-trifluorobenzenemethanol

Obtained by carrying out the reaction as in Example $I_6$ but starting from 1-bromo-2,4,5-trifluorobenzene. Yd: 74%

$^1$H N.M.R. (CDCl$_3$):δ=3.5 (1H, broad s, exchangeable with CF$_3$-COOD), 5.0 to 6.5 (4H, m), 6.7 to 7.6 (1H, m).

EXAMPLE $I_8$ (Method I'')

α-Ethenyl-2,3,5-trifluorobenzenemethanol

A solution of 4.1 g (0.0194 mol) of 1-bromo-2,3,5-trifluorobenzene in 50 ml of anhydrous ether is cooled to −76 ° C. under a nitrogen atmosphere. 12.1 ml (0.0194 mol) of a 1.6M solution of n-butyllithium in hexane are added dropwise over 15 minutes at a temperature below −72° C. The mixture is stirred for 2 minutes at −73° C. and then a solution of 1.15 g (0.0205 mol) of acrolein in 5 ml of anhydrous ether is added dropwise. The mixture is stirred for 30 minutes at −70° C. and is then allowed to return to room temperature. The mixture is poured onto a mixture of 100 g of ice and 10 g of concentrated H$_2$SO$_4$. Extraction with ether, washing with water, drying over Na$_2$SO$_4$, filtration and concentration under vacuum are carried out. The residue obtained is used without other purification in the following stage. Weight obtained: 3.1 g (Yd.=86%)

$^1$H N.M.R. (CDCl$_3$):δ=3.5 (1H, broad s, exchangeable with CF$_3$-COOD), 5.0 to 6.5 (4H, m), 6.5 to 7.3 (2H, m).

EXAMPLE J (Method J)

4-Bromo-1-fluoro-2-(1-propenyl)benzene (E+Z)

A mixture of 16.5 g (0.044 mol) of ethyltriphenylphosphonium bromide and 387 ml of anhydrous THF is cooled to −50° C. under a nitrogen atmosphere. 27.8 ml (0.044 mol) of a 1.6M solution of n-butyllithium in hexane are added dropwise. The mixture is allowed to return to 0° and is stirred for 1 h at 0° C. The mixture is cooled to −30° C. and a solution of 8.8 g (0.0433 mol) of 5-bromo-2-fluorobenzaldehyde in 43 ml of anhydrous THF is added dropwise. The mixture is stirred overnight at room temperature and then for 2 h at 40° C. Filtration is carried out and the filtrate is evaporated under vacuum.

The residue is purified by chromatography on silica (eluent: 10/1 hexane/ethyl acetate). Yd.: 4,1 g (45%)

$^1$H N.M.R. (CDCl$_3$):1.6 to 2.1 (3H, m), 5.5 to 6.5 (2H, m), 6.5 to 7.7 (3H, m) (mixture of E and Z isomers).

EXAMPLE K (Method K)

(E)-4-Bromo-1-fluoro-2-(1-propenyl)benzene

A mixture of 4.1 g (0.019 mol) of the above E+Z isomers, 350 ml of hexane and 0.1 g of iodine is stirred for 5 days at room temperature. Washing with an aqueous NaHCO$_3$ solution, then with an aqueous sodium thiosulphate solution and then with water is carried out. Drying over Na$_2$SO$_4$, filtration and evaporation under vacuum are carried out. The residue is used without other purification in the following stage. Yd.: 3.9 g (95 %)

$^1$H N.M.R. (CDCl$_3$):1.85 (3H, d), 6.0 to 8.0 (5H, m).

EXAMPLE L (Method L)

Methyl 3-(4-bromo-2-fluorophenyl)-2-propenoate

A mixture of 19.3 g (0.095 mol) of 4-bromo-2-fluorobenzaldehyde (prepared according to U.S. Pat. No. 3,904,654), 15.1 g (0.145 mol) of malonic acid, 45 ml of pyridine and 1.2 ml of piperidine is heated for 3 h at reflux. The mixture is poured into 600 ml of water and acidified with concentrated HCl.

The precipitate obtained is filtered, washed with water and dried under vacuum. Yd.: 17.2 g (73%). M.p.= 198°–200° C.

$^1$H N.M.R. (d$_6$-DMSO): 6.55 (1H, d, J=18 Hz), 7.25 to 8.0 (4H, m), 12.5 (1H, s, exchangeable with CF$_3$COOD).

The 3-(4-bromo-2-fluorophenyl)-2-propenoic acid obtained (17.1 g, 0.0698 mol) is taken up in 250 ml of methanol and 0.5 ml of concentrated sulphuric acid and heated for 12 h at reflux. Evaporation is carried out under vacuum and the residue purified by chromatography on silica (eluent: 1/1 hexane/ethyl acetate). Yd.: 14.7 g (81%) M.p. : 63°–65° C.

$^1$H N.M.R. (CDCl$_3$):3.77 (3H, s), 6.45 (1H, d, J=17 Hz), 7.1 to 7.5 (3H, m), 7.7 (1H, d, J=17 Hz).

EXAMPLE M$_1$ (Method M)

Ethyl 3-(2,4-dichlorophenyl)-2-methyl -2-propenoate

A mixture of 22.4 g (0.128 mol) of 2,4-dichlorobenzaldehyde, 2.0 ml of THF and 52.5 g (0.144 mol) of ethyl 2-(triphenylphosphoranylidene) propanoate (prepared according to O. Isler et al., Helv. Chim. Acta, 1957, 40, 1242) is heated for 7 h at reflux. The THF is evaporated under vacuum, the residue is taken up in 700 ml of ether, filtration is carried out, the solid is washed with ether, the filtrate is evaporated under vacuum and the residue is distilled. Weight obtained: 31.3 g (Yd.=94%). B.P.$_{0.3\ mm\ Hg}$=115°–120° C.

$^1$H N.M.R. (CDCl$_3$):1.3 (3H, t), 1.9 (2H, d), 4.2 (2H, q), 7.0 to 7.6 (4H, m)

EXAMPLE M$_2$ (Method M')

Ethyl 2-fluoro-3-[3-(trifluoromethyl)phenyl]-2-propenoate (E+Z)

1.7 g (0.0425 mol) of sodium hydride, as a 60% suspension in oil, are added portionwise over 10 min to a solution of 10.1 g (0.0417 mol) of ethyl (diethoxyphosphoryl) fluoroacetate (prepared according to E. Elkik and M. Imbeaux, Synthesis, 1989, p. 861) in 80 ml of 1,2-dimethoxyethane, the temperature being maintained below 35° C. The mixture is then stirred for 30 min at room temperature, 6.9 g (0.0396 mol) of 3-(trifluoromethyl)benzaldehyde are then added dropwise and the mixture is then heated for 4 h at reflux. The mixture is poured into water and extraction with ether, washing with water, drying over Na$_2$SO$_4$, filtration and evaporation of the ether under vacuum are carried out. The residue obtained (10.3 g, quantitative Yd.) is used without other purification in the following stage.

$^1$H N.M.R. (CDCl$_3$):1.0 to 1.6 (3H, m), 3.9 to 4.6 (2H, m), 6.5 to 8.0 (5H, m).

EXAMPLE M$_3$

Ethyl 2-fluoro-3-[2-fluoro-3-(trifluoromethyl)phenyl]-2-propenoate (E+Z)

Obtained by carrying out the reaction as in Example M$_2$ but starting from 2-fluoro-3-(trifluoromethyl) benzaldehyde (itself obtained according to the process of Patent EP 225, 175). Yd.=98%

$^1$H N.M.R. (CDCl$_3$):1.0 to 1.6 (3H, m), 4.0 to 4.5 (2H, m), 6.5 to 8.2 (4H, m)

EXAMPLE N$_1$ (Method N)

Methyl 3-(3-bromo-5-fluorophenyl)-2-propenoate

A mixture of 5.1 g (0.02 mol) of 1,3-dibromo-5- fluorobenzene (prepared according to A. Cannoni de Degiorgi and E. V. Zappi, Anales asoc. quim. argentina, 1940, 28, 72) (C. A. 34 6593$^3$), 2.2 ml (0.025 mol) of methyl acrylate, 10 ml of triethylamine, 0.044 g (0.002 mol) of palladium acetate and 0.208 g (0.0008 mol) of triphenylphosphine is heated for 24 h at 100° C. in a closed vessel with magnetic stirring. Cooling, pouring into 1N HCl, extraction with ether, washing with water, drying over Na$_2$SO$_4$, filtration and evaporation under vacuum are carried out. The residue is purified by chromatography on silica (eluent: 2/1 hexane/ethyl acetate). Yd.: 2.7 g (51%) M.p.=95°–6° C.

$^1$H N.M.R. (CDCl$_3$): 3.77 (3H, s), 6.35 (1H, d, J=15 Hz), 6.95 to 7.7 (4H, m).

EXAMPLE N$_2$

Methyl 3-[4-chloro-3-(trifluoromethyl)phenyl]-2-propenoate

By carrying out the reaction as in example N$_1$, but starting from 4-bromo-1-chloro-2-trifluoromethylbenzene, methyl 3-[4-chloro-3-(trifluoromethyl)phenyl]-2-propenoate is obtained. Yd.: 74% M.p.:71°–73° C.

$^1$H N.M.R. (CDCl$_3$):3.77 (3H, s), 6.4 (1H, d, J=16 Hz), 7.1 to 7.9 (4H, m)

Example P (Method P)

2-Fluoro-5-(trifluoromethyl)benzaldehyde

A mixture of 18.7 g (0.0988 mol) of 2-fluoro-5-(trifluoromethyl)benzonitrile (prepared according to G. C. Finger et al., Chem. Comm., 1965, 430), 398 ml of 90% formic acid, 296 ml of water and 17.5 g of Raney nickel is heated for 5 hours at reflux and is then left standing overnight. The mixture is poured into 2.5 liters of water and extraction is carried out with methylene chloride (once 1 l and two times 500 ml). Filtration, washing with water, drying over $Na_2SO_4$, filtration and distillation are carried out. Yd.: 10.1 g (53%) B.p.$_{14}$=70°–72° C. IR: $\nu_{c-o}$=1680 $cm^{-1}$ $^1$H N.M.R. ($CDCl_3$): 7.0 to 8.3 (3H, m), 10.25 (1H, s).

EXAMPLE $Q_1$ (Method Q)

5-Bromo-2-fluorobenzaldehyde

A mixture of 79.5 g (0.296 mol) of 4-bromo-2-bromomethyl-1-fluorobenzene (prepared according to G. E. Stokker, A. W. Alberts et al., J. Med. Chem., 1986, 29, 170), 126 ml of acetic acid, 82.7 g (0.59 mol) of hexamethylenetetramine and 126 ml of water is heated for 2 hours at reflux. The mixture is cooled to 90° C., 99.5 ml of concentrated hydrochloric acid are added and the mixture is heated for 30 min at reflux. Cooling, extraction with ether, washing with water, washing with an aqueous $NaHCO_3$ solution, washing with water, drying over $Na_2SO_4$, filtration and evaporation under vacuum are carried out. The residue is purified by chromatography on silica (eluent: 10/1 hexane/ethyl acetate). Yd.: 23.6 g (39%)

$^1$H N.M.R. ($CDCl_3$): 6.8 to 8.1 (3H, m), 10.3 (1H, s).

EXAMPLE $Q_2$

3-Bromo-2-fluorobenzaldehyde

Obtained by carrying out the reaction as in Example $Q_1$ but starting from 1-bromo-3-bromomethyl-2-fluorobenzene. Yd.: 59%

$^1$H N.M.R. ($CDCl_3$): 6.8 to 8.0 (3H, m), 10.3 (1H, s).

EXAMPLE R (Method R)

1-Bromo-3-bromomethyl-2-fluorobenzene

Obtained according to Example E but starting from 1-bromo -2-fluoro- 3-methylbenzene (prepared according to M. S. Newman and R. Kannan, J. Org. Chem., 1976, 41, 3356 ) and distilling the final product at 20 mm Hg. Yd.: 66% B.p.$_{20}$=95°–105° C.

$^1$H N.M.R. ($CDCl_3$): 4.4 (2H, s), 6.6 to 7.6 (3H, m).

EXAMPLE S (Method S)

3-Fluoro-3-[3-(trifluoromethyl)phenyl]-2-propenoic acid (E+Z)

A mixture of 190 ml of anhydrous THF and 48 ml of anhydrous ether is cooled to –80° C. under a nitrogen atmosphere. Sparging is carried out with 1,1-difluoroethylene until 5.2 g (0.0796 mol) have been absorbed. The mixture is cooled to –115° C. and 54.7 ml (0.0765 mol) of a 1.4M solution of secondary butyllithium in cyclohexane are added dropwise over 15 min. The mixture is allowed to react for 10 min at –100° C. The mixture is cooled to –105° C., sparging is carried out with carbon dioxide gas for 20 minutes at –105° C. and the mixture is then allowed to react for 15 min at –110° C. Sparging is then carried out with a nitrogen stream, while allowing to return to room temperature, and the mixture is left for 1 h at 10° C. with nitrogen sparging. The mixture is again cooled to –75° C. and a 3-(trifluoromethyl) phenylmagnesium bromide solution (prepared from 39.4 g (0.175 mol) of 3-bromo-1-(trifluoromethyl)benzene, 3.9 g (0.160 mol) of magnesium, 120 ml of anhydrous ether and an iodine crystal) is added dropwise and the mixture is then allowed to react for 1 hour at –40° C. Hydrolysis is carried out by slow addition of 6N sulphuric acid and extraction with ether, washing with water, drying over $Na_2SO_4$, filtration and evaporation under vacuum are carried out. The residue is taken up in ether and extracted with an aqueous $NaHCO_3$ solution. The aqueous phase is acidified with 6N HCl and extracted with $CH_2Cl_2$; drying over $Na_2SO_4$, filtration and evaporation under vacuum are carried out. The mixture of E+Z isomers obtained is used without other purification in the following stage ($F_{10}$). Weight obtained: 2.5 g (Yd.: 13%)

$^1$H N.M.R. ($d_6$-DMSO): 5.8 to 6.8 (1H, m), 7.5 to 8.2 (4H, m), 12.5 (1H, broad s, exchangeable with $CF_3$-COOD).

EXAMPLE T (Method T)

Sodium (E) -3-[3-[2-fluoro-3-(trifluoromethyl)phenyl]-2-propenyl]-3,4-dihydro-4-oxo-1-phthalazineacetate A solution of 1.52 g (0. 0369 mol) of sodium hydroxide, as pellets (97%), in 3 ml of water and 60 ml of ethanol is added to a solution of 15 g (0.0369 mol) of (E) -3-[3-[2-fluoro-3-(trifluoromethyl)phenyl]-2propenyl]- 3,4-dihydro-4-oxo-1-phthalazineacetic acid in 600 ml of ethanol, the mixture is stirred for 15 min at room temperature and is then evaporated under vacuum. The residue is triturated in anhydrous ether, filtered, washed with anhydrous ether, dried for 5 h at 70° C. under vacuum and recrystallized from isopropanol. Weight obtained: 14.2 g (Yd.: 89%). M.p.=170°–175° C. Elemental analysis: $C_{20}H_{13}F_4N_2NaO_3$ (M=428.317).

| Elemental analysis: $C_{20}H_{13}F_4N_2NaO_3$ (M = 428.317). | | | | | |
|---|---|---|---|---|---|
| | C % | H % | F % | N % | Na % |
| Calculated | 56.08 | 3.06 | 17.74 | 6.54 | 5.37 |
| Found | 56.08 | 2.85 | 17.69 | 6.66 | 5.44 |

$^1$H N.M.R.: 3.6 (2H, s), 4.8 to 5.0 (2H, m), 6.6 to 6.75 (2H, m), 7.0 to 8.3 (7H, m).

We claim:

1. A 3,4-dihydro-4-oxo- 3-(2-propenyl)-1-phthalazine compound of formula I:

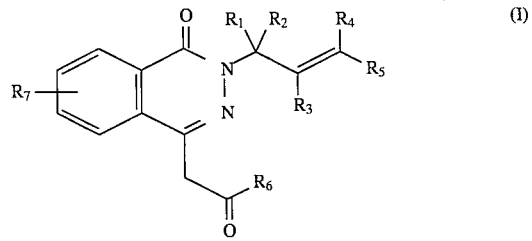

in which $R_1$, $R_2$ and $R_3$, which are identical or different are selected from the group consisting of hydrogen, halogen and $C_1$–$C_4$ alkyl;

$R_4$ and $R_5$, which are different, are selected from the group consisting of hydrogen; halogen; $C_1$–$C_4$ alkyl; phenyl; phenyl substituted by 1 to 5 substituents selected from the group consisting of halogen, $C_1$–$C_4$ alkyl and trifluoromethyl; a heterocyclic group selected from thienyl, pyrrolyl and furyl; and said heterocyclic group substituted by 1 to 5 substituents selected from the group consisting of halogen, $C_1$–$C_4$ alkyl and trifluoromethyl;

$R_6$ is selected from the group consisting of hydroxyl and $C_1$–$C_4$ alkoxy;

$R_7$ is selected from the group consisting of hydrogen, halogen, $C_1$–$C_4$ alkyl and $C_1$–$C_4$ alkoxy, and its pharmaceutically acceptable salt.

2. Compound according to claim 1, wherein $R_7$ represents hydrogen.

3. Compound according to claim 1, wherein $R_6$ is selected from the group consisting of OH and $OC_2H_5$.

4. Compound according to claim 1, wherein $R_1$, $R_2$ and $R_3$ are selected from the group consisting of H, $CH_3$ and F.

5. Compound according to claim 1, wherein one of $R_4$ and $R_5$ is selected from the group consisting of phenyl; phenyl substituted by 1 to 5 substituents selected from the group consisting of halogen, $C_1$–$C_4$ alkyl and trifluoromethyl; a heterocyclic group selected from thienyl, pyrrolyl and furyl; and said heterocyclic group substituted by 1 to 5 substituents selected from the group consisting of halogen, $C_1$–$C_4$ alkyl and trifluoromethyl, the other of $R_4$ and $R_5$ being selected from the group consisting of H and $C_1$–$C_4$ alkyl.

6. Compound according to claim 1, wherein $R_4$ or $R_5$ is selected from the group consisting of thienyl and thienyl substituted by a group selected from halogen and $C_1$–$C_4$ alkyl.

7. Compound according to claim 1, selected from (E)-3-[3-[2-fluoro-3-(trifluoromethyl)phenyl]-2-propenyl- 3,4-dihydro-4-oxo-1-phtalazineacetic acid;

(Z)-3-[2-fluoro-3-[3-(trifluoromethyl)phenyl]-2-propenyl]-3,4-dihydro-4-oxo-1-phtalazineacetic acid;

(E)-3-[3-[2,3,5-trifluorophenyl]-2-propenyl]-3,4-dihydro- 4-oxo-1-phtalazineacetic acid;

(E)-3-[3-[2,3,6-trifluorophenyl]-2-propenyl]-3,4-dihydro- 4-oxo-1-phtalazineacetic acid;

(E)-3-[3-[3-bromo-2,6-difluorophenyl)-2-propenyl]-3,4-dihydro- 4-oxo-1-phtalazineacetic acid;

(E)-3-[3-[2,6-difluoro-3-(trifluoromethyl)phenyl]-2-propenyl]- 3,4-dihydro-4-oxo-1-phtalazineacetic acid;

(E)-3-[3-[2,3,5,6-tetrafluorophenyl]-2-propenyl]-3,4-dihydro- 4-oxo-1-phtalazineacetic acid; and (Z)-3-[2-fluoro-3-[2-fluoro-3-(trifluoromethyl)phenyl]-2-propenyl]-3,4-dihydro-4-oxo-1-phtalazineacetic acid.

8. Pharmaceutical composition containing a pharmaceutically acceptable carrier, and as active ingredient a compound according to claim 1, in an amount effective for the treatment of diabetic nephropathies, neuropathies, retinopathies or cataracts.

9. A process for the treatment of a pathology requiring the inhibition of aldose reductase comprising administering to a man in need thereof an effective amount of a compound according to claim 1, associated with a pharmaceutically acceptable carrier.

10. A process for the treatment of diabetic nephropathies, neuropathies, retinopathies or cataracts comprising administering to a man in need thereof an effective amount of a compound according to claim 1, associated with a pharmaceutically acceptable carrier.

* * * * *